US011060964B2

(12) United States Patent
Kaneko

(10) Patent No.: US 11,060,964 B2
(45) Date of Patent: Jul. 13, 2021

(54) CELL DETECTION METHOD

(71) Applicant: FUJIFILM Corporation, Tokyo (JP)

(72) Inventor: Yasuhisa Kaneko, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 212 days.

(21) Appl. No.: 16/124,417

(22) Filed: Sep. 7, 2018

(65) Prior Publication Data

US 2019/0003953 A1 Jan. 3, 2019

Related U.S. Application Data

(63) Continuation of application No. PCT/JP2017/005329, filed on Feb. 14, 2017.

(30) Foreign Application Priority Data

| Mar. 30, 2016 | (JP) | JP2016-068198 |
| Jun. 9, 2016 | (JP) | JP2016-115038 |

(51) Int. Cl.

| C12Q 1/686 | (2018.01) |
| G01N 15/14 | (2006.01) |
| G01N 21/64 | (2006.01) |
| G01N 33/49 | (2006.01) |
| G01N 21/53 | (2006.01) |
| G01N 33/537 | (2006.01) |
| G01N 33/53 | (2006.01) |
| G01N 33/533 | (2006.01) |
| G01N 33/569 | (2006.01) |
| G01N 15/10 | (2006.01) |
| G01N 15/00 | (2006.01) |

(52) U.S. Cl.
CPC ......... *G01N 15/1463* (2013.01); *C12Q 1/686* (2013.01); *G01N 15/1404* (2013.01); *G01N 15/1429* (2013.01); *G01N 15/1459* (2013.01); *G01N 15/1468* (2013.01); *G01N 21/53* (2013.01); *G01N 21/64* (2013.01); *G01N 21/6428* (2013.01); *G01N 21/6452* (2013.01); *G01N 33/49* (2013.01); *G01N 33/4915* (2013.01); *G01N 33/533* (2013.01); *G01N 33/5304* (2013.01); *G01N 33/537* (2013.01); *G01N 33/56966* (2013.01); *G01N 2015/0065* (2013.01); *G01N 2015/1006* (2013.01); *G01N 2015/149* (2013.01); *G01N 2015/1461* (2013.01)

(58) Field of Classification Search
CPC .............. G01N 33/533; G01N 33/537; G01N 33/56966; G01N 15/1463; G01N 15/1404; G01N 15/1459; G01N 15/1468; G01N 21/53; G01N 21/64; G01N 21/6428; G01N 21/6452; G01N 33/4915; G01N 33/5304; G01N 2015/148; G01N 2015/1461; G01N 2015/1006; G01N 2015/0065; C12Q 1/686
See application file for complete search history.

(56) References Cited

U.S. PATENT DOCUMENTS

2010/0255471 A1* 10/2010 Clarke ................. C12Q 1/6886
435/6.14
2014/0146157 A1 5/2014 Duplisea et al.

FOREIGN PATENT DOCUMENTS

| CN | 102333891 A | 1/2012 |
| CN | 104486549 A | 4/2015 |
| JP | 2000-157298 A | 6/2000 |
| JP | 2012-515533 A | 7/2012 |

OTHER PUBLICATIONS

Evans et al. (Assurance of Monoclonality in One round of Cloning Through Cell Sorting for Single Cell Deposition Coupled with High Resolution Cell Imaging. The Authors Biotechnology Progress. AICE. 31 (5): 1172-1178 (Sep. 18, 2015).*
Krista Evans et al., "Assurance of Monoclonality in One round of Cloning Through Cell Sorting for Single Cell Deposition Coupled with High Resolution Cell Imaging," The Authors Biotechnology Progress, 2015, pp. 1172-1178, vol. 31, No. 5.
Susanne T. Gren et al., "A Single-Cell Gene-Expression Profile Reveals Inter-Cellular Heterogeneity within Human Monocyte Subsets," PLOS ONE, Dec. 9, 2015, pp. 1-20.
Michael S. Zordan et al., "Photoablative dilution with pre-enrichment for the clonal isolation of rare cancer cells." Proc. SPIE, vol. 7182 (2009) pp. 71820z.1-71820z.7.
International Search Report of PCT/JP2017/005329 dated May 16, 2017 [PCT/ISA/210].
Written Opinion of the ISA issued in International Application No. PCT/JP2017/005329 dated May 16, 2017 [PCT/ISA/237].
International Preliminary Report on Patentability issued in International Patent No. PCT/JP2017/005329 dated Oct. 2, 2018 [PCT/IB/373].
Communication dated Aug. 23, 2019, from the Japanese Patent Office in counterpart application No. 2018-508537.
Communication dated Apr. 30, 2021, from the China National Intellectual Property Administration in application No. 201780019613.1.

* cited by examiner

*Primary Examiner* — Gailene Gabel
(74) *Attorney, Agent, or Firm* — Sughrue Mion, PLLC

(57) ABSTRACT

Provided is a cell detection method which makes it possible to effectively and accurately perform gene analysis only on target cells. The cell detection method includes a sorting step of obtaining first information derived from cells in a sample solution by using a flow cytometry method and sorting target cells into a container having arrays of wells each having an opening based on the first information, an imaging step of imaging the cells sorted into the container, and a determination step of obtaining second information derived from cells based on the image of the cells captured by the imaging step and determining cells to be analyzed from the sorted cells.

20 Claims, 8 Drawing Sheets

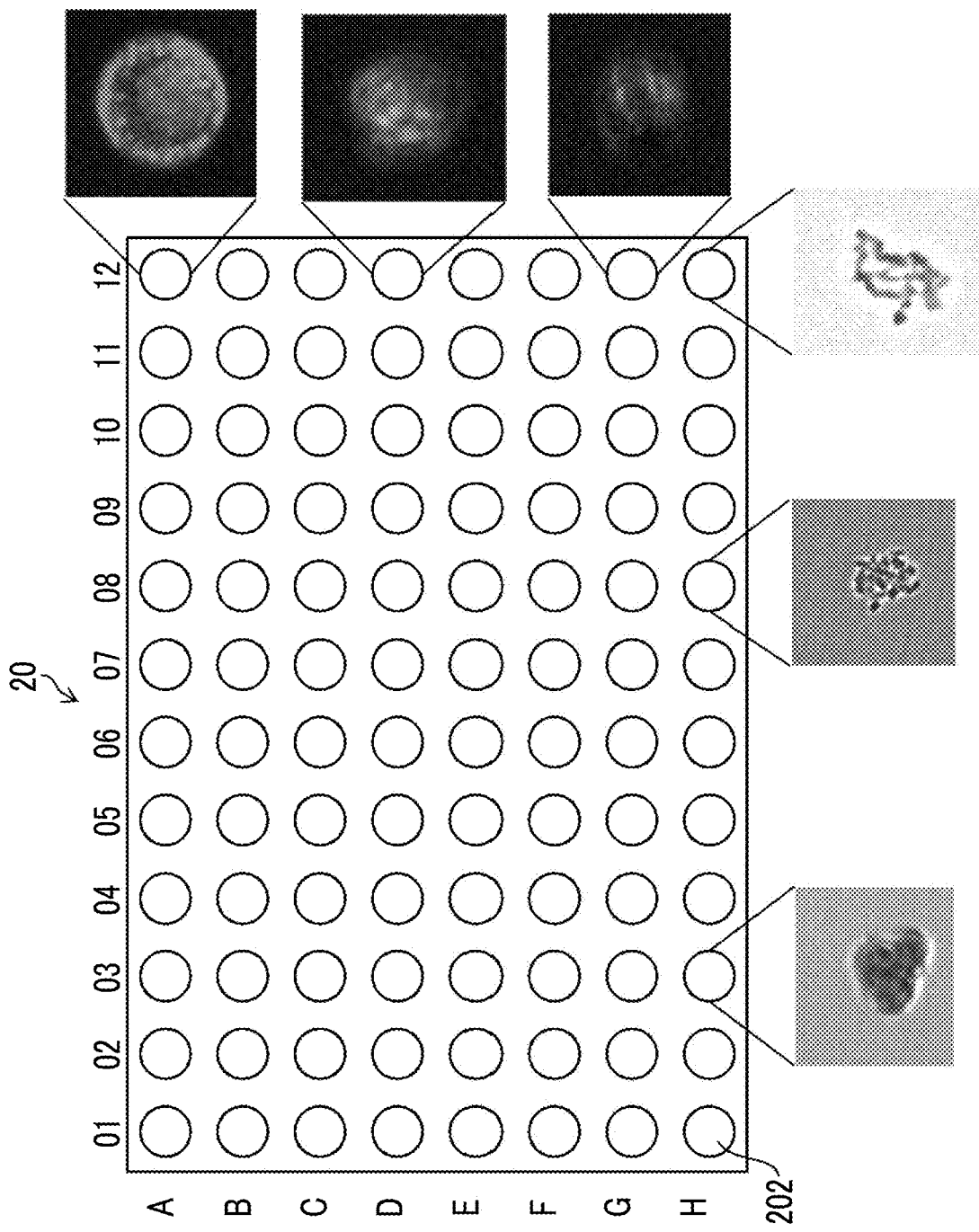

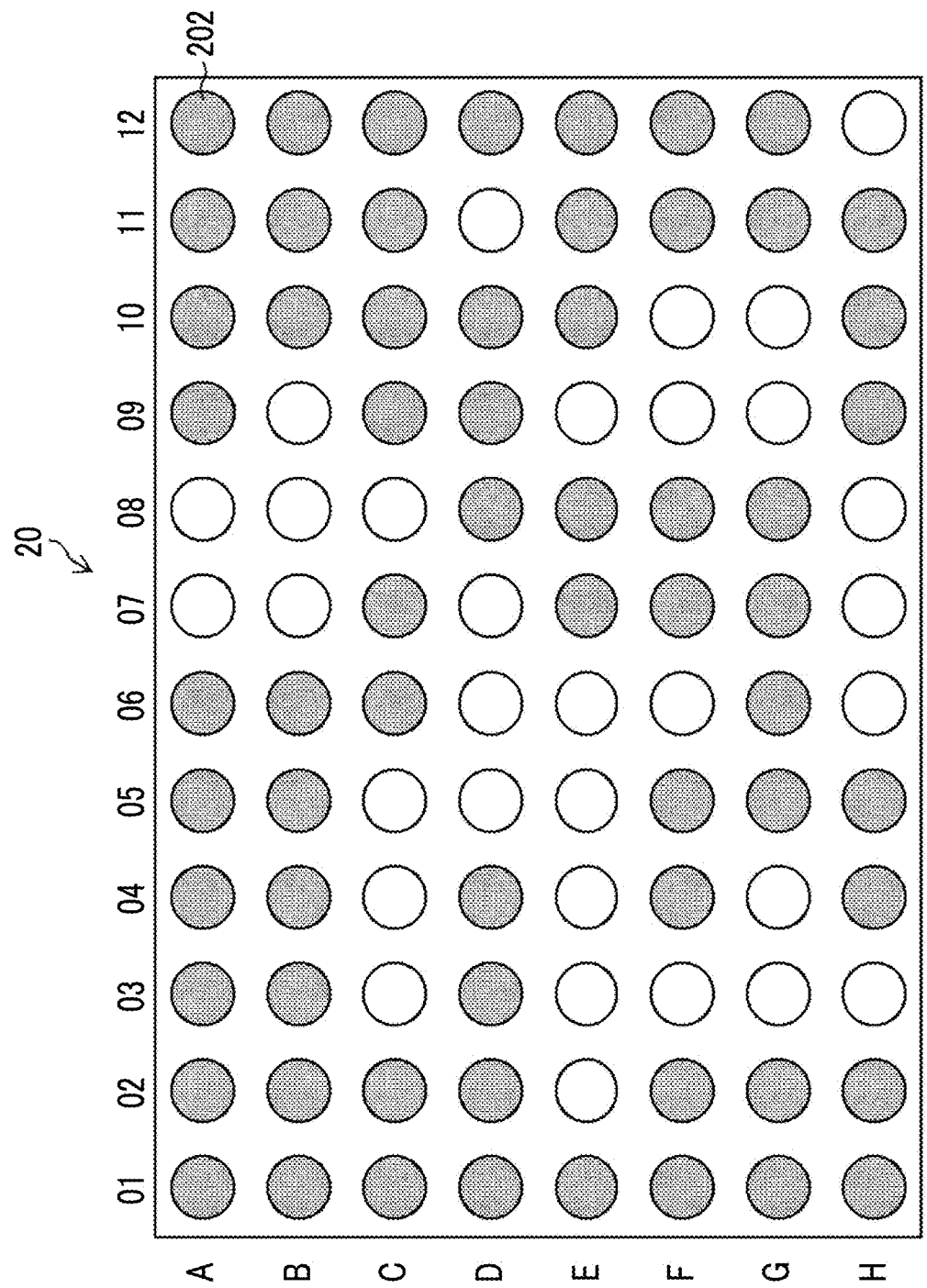

CELL DETECTION METHOD

CROSS REFERENCE TO RELATED APPLICATIONS

This application is a Continuation of PCT International Application No. PCT/JP2017/005329 filed on Feb. 14, 2017, which claims priority under 35 U.S.C § 119(a) to Patent Application No. 2016-068198 filed in Japan on Mar. 30, 2016, and Patent Application No. 2016-115038 filed in Japan on Jun. 9, 2016 all of which are hereby expressly incorporated by reference into the present application.

BACKGROUND OF THE INVENTION

1. Field of the Invention

The present invention relates to a cell detection method.

2. Description of the Related Art

A method is known in which target cells are separated and collected from a sample solution by using a flow cytometry method.

For example, JP2000-157298A describes a method for collecting tiny cells (micronucleus), which are a portion of cells separated due to chromosomal abnormalities, by dividing the cells into main nucleus (parent nucleus) and micronucleus by using a sorting function of a flow cytometer (device used in a flow cytometry method).

SUMMARY OF THE INVENTION

In the flow cytometry method, the information such as forward-scattered light, side-scattered light, and fluorescence intensity is obtained from cells so as to select cells, and target cells are sorted into a container having a plurality of wells such that one cell is dispensed into one well. The container into which the cells are sorted is set in a Polymerase Chain Reaction (PCR) device, Deoxyribonucleic Acid (DNA) is amplified, and gene analysis is performed.

In the flow cytometry method, target cells are sorted based on the information on fluorescence intensity. Therefore, cells are missorted in some cases due to the nonspecificity of staining. Furthermore, in some cases, two or more cells are sorted into one well.

It is considered that performing DNA amplification and gene analysis on the container having the aforementioned problems is ineffective and affects the accuracy of the gene analysis.

The present invention has been made in consideration of the above circumstances, and an object thereof is to provide a cell detection method which makes it possible to effectively and accurately perform gene analysis only on target cells.

According to an aspect of the present invention, a cell detection method comprises a sorting step of obtaining first information derived from cells in a sample solution by using a flow cytometry method and sorting target cells into a container having arrays of wells each having an opening based on the first information, an imaging step of imaging the cells sorted into the container, and a determination step of obtaining second information derived from cells based on the image of the cells captured by the imaging step and determining cells to be analyzed from the sorted cells.

It is preferable that the cell detection method further comprises a step of staining cells before the sorting step.

It is preferable that the container has arrays of a plurality of wells each having an opening.

It is preferable that the imaging step includes a step of moving the cells to a bottom surface of each of the wells by centrifugation.

It is preferable that the imaging step includes a step of imaging the cells sorted into the container from a side opposite to the opening of each of the wells of the container.

It is preferable that the sorting step includes a step of correlating a position of each of the wells with the first information with, and the determination step includes a step of correlating the position of each of the wells and the first information that are correlated with each other with the second information.

It is preferable that the first information includes at least one of forward-scattered light, side-scattered light, or fluorescence, and the second information includes at least one of fluorescence, a cell shape, a transmitted color, or a size.

It is preferable that the sample solution contains blood cells.

It is preferable that the wells of the container are arrayed in rows and columns.

It is preferable that the cell detection method further comprises an isolation step of isolating only the cells to be analyzed from the container after the determination step.

It is preferable that in the isolation step, only the cells to be analyzed are isolated using a capillary or a pipette.

It is preferable that the cells isolated in the isolation step are moved to a tube for PCR or a plate for PCR.

It is preferable that the first information and the second information are correlated with positional information of the tube for PCR or the plate for PCR.

It is preferable that the container contains a culture solution in the interior thereof.

It is preferable that the culture solution contains at least one staining solution.

It is preferable that the cell detection method further includes a step of substituting the culture solution with a culture solution containing no staining solution after the imaging step.

According to the cell detection method of the present invention, it is possible to effectively and accurately perform gene analysis only on target cells.

BRIEF DESCRIPTION OF THE DRAWINGS

FIG. 8 is a plan view of the container having undergone an imaging step.

FIG. 9 is a plan view of the container in which the wells containing cells to be analyzed are colored.

DESCRIPTION OF THE PREFERRED EMBODIMENTS

Figure 1:
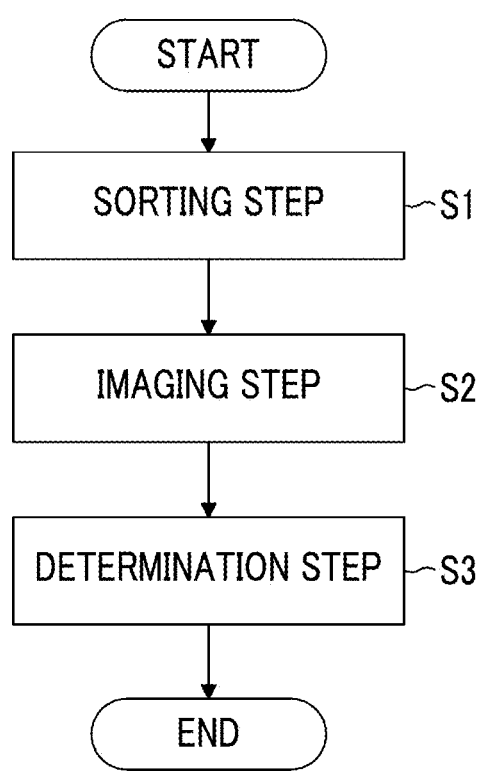
FIG. 1 is flowchart showing the procedure of a cell detection method.

Hereinafter, preferred embodiments of the present invention will be described based on the attached drawings. The present invention will be described based on the following preferred embodiments. The present invention can be modified by many techniques without departing from the scope of the present invention, and embodiments other than the above embodiments can be used. Accordingly, all of the modifications in the scope of the present invention are included in claims.

In the drawings, the portions represented by the same references are the same constituents having the same function. Furthermore, in the present specification, in a case where a range of numerical values is represented using "to", the numerical values as the upper limit and the lower limit represented by "to" are also included in the range of numerical values.

<Cell Detection Method>

A cell detection method of the present embodiment will be described with reference to drawings. In the present embodiment, the cell detection method will be described by illustrating a case where blood cells are contained in a sample solution and nucleated erythrocytes are target cells.

FIG. 1 is a flowchart of the cell detection method of the present embodiment. As shown in FIG. 1, the cell detection method includes at least a sorting step (step S1), an imaging step (step S2), and a determination step (step S3).

In the sorting step (step S1), first information derived from cells in the sample solution is obtained by a flow cytometry method, and target cells are sorted into a container having arrays of wells each having opening based on the first information. In the imaging step (step S2), the cells sorted into the container are imaged. In the determination step (step S3), based on the image of the cells captured by the imaging step, second information derived from cells is obtained, and cells to be analyzed are determined from the sorted cells based on the second information. Hereinafter, each of the steps will be described.

<Sorting Step>

In the sorting step, first information derived from the cells in the sample solution is obtained using a flow cytometer 10 performing a flow cytometry method, and cells are sorted into a container.

Figure 2:
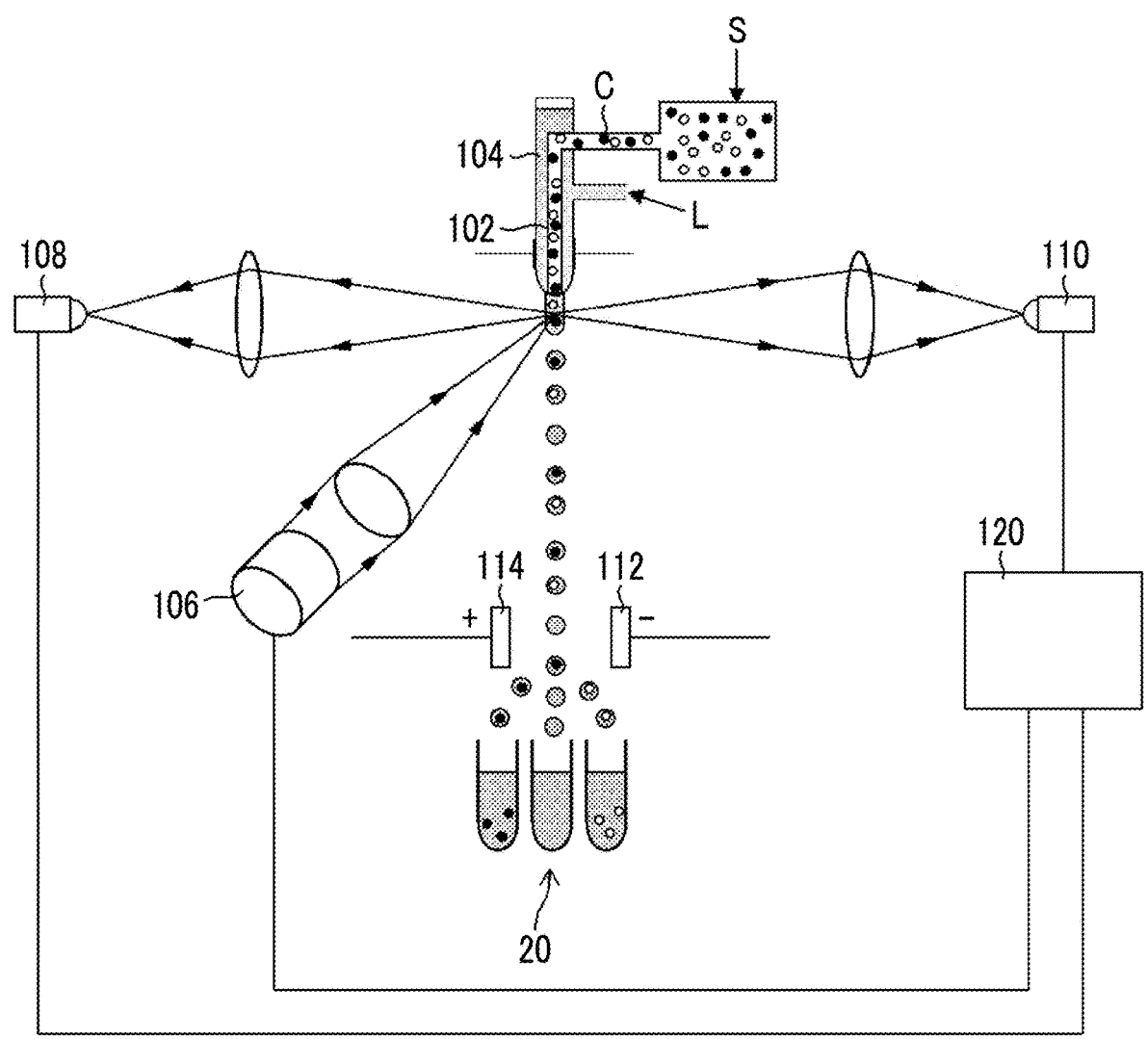
FIG. 2 is a conceptual view of a flow cytometer.

FIG. 2 is a conceptual view of the flow cytometer 10. A sample solution S contains blood cells including cells C immunostained by an antigen-antibody reaction.

The antigen-antibody reaction refers to a reaction in which an antibody specifically binds to an antigen having a complementary structure, and the immunostaining means a technique of causing a fluorescent label-conjugated antibody to bind to an antigen present in a cell.

The immunostaining includes a direct method and an indirect method. The direct method is a method of directly conjugating a fluorescent label to an antibody and causing the antibody to react with an antigen. In contrast, the indirect method is a method of conjugating a fluorescent label not to an antibody (primary antibody) which can specifically bind to an antigen which should be detected but to an antibody (secondary antibody) which can specifically bind to the primary antibody so as to detect the antigen.

In order to obtain the first information derived from cells the flow cytometer 10, the cells are immunostained by the antigen-antibody reaction as described above. Examples of anti-human CD antibodies include an anti-CD3 antibody, an anti-CD4 antibody, an anti-CD14 antibody, an anti-CD25 antibody, and an anti-CD127 antibody. Examples of the fluorescent label include 4',6-diamidine-2'-phenylindole dihydrochloride (DAPI: 4',6-diamidino-2-phenylindole), propidium iodide (PI), Pyronin Y, fluorescein isothiocyanate (FITC), phycoerythrin (PE), allophycocyanin (APC), Texas Red (TR (registered trademark)), Hoechst 33342, 7-aminoactinomycin D (7-AAD), 2'-deoxycytidine 5'-triphosphoric acid (Cy3), sulfoindocyanine succinimidyl ester (Cy5), DRAQ5 (registered trademark) (manufactured by BioStatus Limited), Brilliant Violet 570, Brilliant Violet 421, and the like.

In order to prevent the cells from being damaged, it is preferable to put a culture solution in advance into the container into which cells will be sorted. As the culture solution, phosphate buffered saline (PBS) or PBS to which 0.1% by mass bovine serum albumin (BSA) is added is preferable. More preferably, in order to prevent the antibodies staining the cells from being separated from the cells, a staining solution is added to the culture solution in advance. It is particularly preferable to add a staining solution in advance that stains the nucleus. For example, in a case where DRAQ5, which is a nucleus staining solution, containing an anthraquinone dye is added in advance, a decrease in fluorescence intensity in the imaging step can be inhibited. The amount of the culture solution is not particularly limited as long as the amount is suitable for the amplification step. In a preferred aspect, an excess of culture solution is added in advance in consideration of the evaporation occurring during the imaging step, and then the culture solution is discarded before the amplification step such that a predetermined amount of culture solution remains.

In a preferred aspect, before the sorting step performed using the flow cytometer, the cells are stained by a staining step. In this case, the sample solution is prepared as below. First, a sample to be analyzed containing target cells is prepared. The sample to be analyzed is mixed, for example, with a hemoclastic and fluorescence-labeled antibodies used for immunostaining and then incubated such that the cells are immunostained. By the immunostaining of the cells, a sample solution S is prepared.

The sample solution S is introduced into a flow cell 104 from a nozzle 102. A sheath liquid L is introduced into the flow cell 104. In the flow cell 104, the sample solution S is squeezed by the sheath liquid L. Because the sample solution S is squeezed, the cells C are arrayed in a line.

The cells C are irradiated, for example, with laser beams from a light source 106. By the irradiation of the laser beams, fluorescent labeling of the cells C by the immunostaining is excited, and the cells C emit fluorescence from the fluorescent label by the immunostaining. The fluorescence intensity is detected by a detector 108. The fluorescence intensity of the cells C detected by the detector 108 is input and stored in a controller 120 as the first information derived from cells. The controller 120 includes an operation unit performing various processes, various programs, a storage unit storing data, and the like.

Scattered light (forward-scattered light, side-scattered light, and the like) from the cells C caused by the radiation of the laser beams from the light source 106 is detected by a detector 110. The fluorescence intensity of the scattered light from the cells C detected by the detector 110 is input and stored in the controller 120 as the first information derived from cells. The size of cells to be measured can be measured by the forward-scattered light, and the structure of cells to be measured and the like can be measured by the side-scattered light and fluorescence.

Ultrasonic waves are applied to the flow cell 104, and hence liquid droplets containing the cell C are formed. Based on the results of the detection described above, the controller 120 causes the liquid droplets to be negatively or positively charged. The controller 120 does not cause liquid droplets, which will be discarded, to be charged. At the time of passing through deflection electrode plates 112 and 114, the charged liquid droplets are attracted to any of the deflection electrode plates 112 and 114. As a result, basically, one cell is sorted into one well in the container 20.

As the light source 106 exciting the immunostaining, a plurality of laser light sources having different wavelengths are preferably used. For example, it is preferable that the flow cytometer includes a laser light source having a wavelength of 405 nm, a laser light source having a wavelength of 488 nm, a laser light source having a wavelength of 561 nm, and a laser light source having a wavelength of 683 nm. In a case where a plurality of laser light sources having different wavelengths are used, a plurality of fluorescence intensities can be obtained as the first information derived from cells.

Furthermore, it is preferable to use a fluorescence filter which cuts the excitation light of laser light sources for simultaneously detecting fluorescence intensities and selectively transmits the wavelength of light emitted from a fluorescent label by immunostaining.

Figure 3:
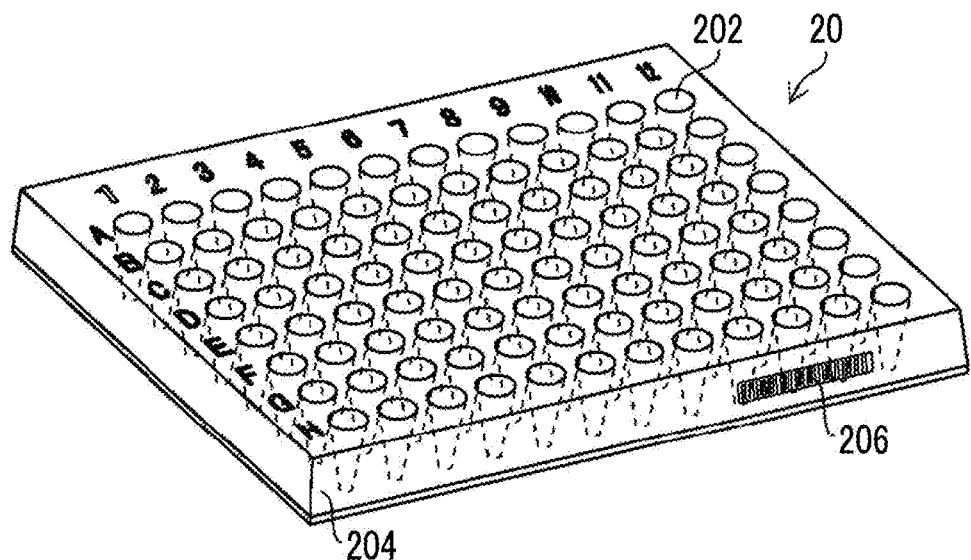
FIG. 3 is a perspective view of a container.
Figure 4:
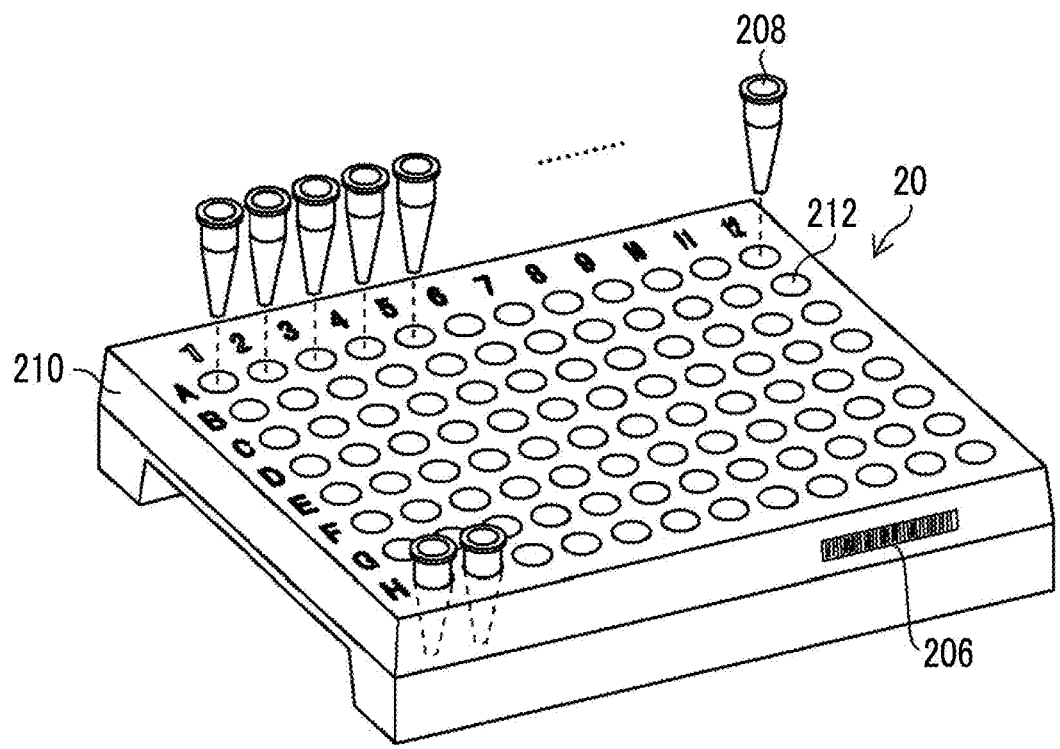
FIG. 4 is a perspective view of a container.

Next, the container into which the cells are sorted will be described. FIGS. 3 and 4 are perspective views of the container 20.

As shown in FIG. 3, the container 20 has a plurality of wells 202 each having an opening and a bottom surface for collecting a plurality of cells and side walls 204 forming an integral structure with the plurality of wells 202. The plurality of wells 202 are arrayed in rows and columns. In order to identify the position of each of the wells 202, numbers representing the rows and alphabets representing the columns are marked on the opening side of the wells 202 of the container 20. In the container 20 shown in FIG. 3, cells are collected into each of the wells 202. In order to identify the container 20, for example, an identification label 206 such as a bar code is marked on the side wall of the container 20.

As shown in FIG. 4, a container 20 having a shape different from that shown in FIG. 3 has a plurality of tubes 208 each having an opening and a bottom surface for collecting a plurality of cells and a supporting member 210 including a plurality of holes 212 for holding the plurality of tubes 208. In the container 20 shown in FIG. 4, the tubes 208 function as wells. As long as the wells each have an opening and a bottom surface for accommodating cells, the shape of the wells and the like are not limited.

The plurality of holes 212 form rows and columns. In order to identify the position of each of the holes 212, numbers representing the rows and alphabets representing the columns are marked on the side, on which the holes 212 are formed, of the container 20. In the container 20 shown in FIG. 4, cells are collected into each of the tubes 208 held in the supporting member 210. Furthermore, in order to identify the container 20, for example, the identification label 206 such as a bar code is marked on the side wall of the supporting member 210. The tubes 208 may be constituted with individual unit tubes or may be constituted with a plurality of tubes connected to each other. In addition, each of the tubes 208 may have a cap (not shown in the drawing).

Because the plurality of wells 202 of the container 20 are arrayed in rows and columns, it is possible to easily identify the positions thereof.

The container 20 has been described by illustrating a container having a plurality of wells 202. However, the container 20 is not limited thereto as long as it has one well 202 into which a cell can be sorted.

The controller 120 of the flow cytometer 10 stores analysis programs for analyzing the detection results based on the first information including the fluorescence intensity of the fluorescence derived from cells and the fluorescence intensity of scattered light. Based on the first information derived from cells, the controller 120 can create a scattergram (scatter plot) in which any of the fluorescence intensity of forward-scattered light, the fluorescence intensity of side-scattered light, and fluorescence intensity is plotted on the ordinate or the abscissa. By creating the scattergram, all of the detected cells can be divided into a plurality of groups.

Figure 5:
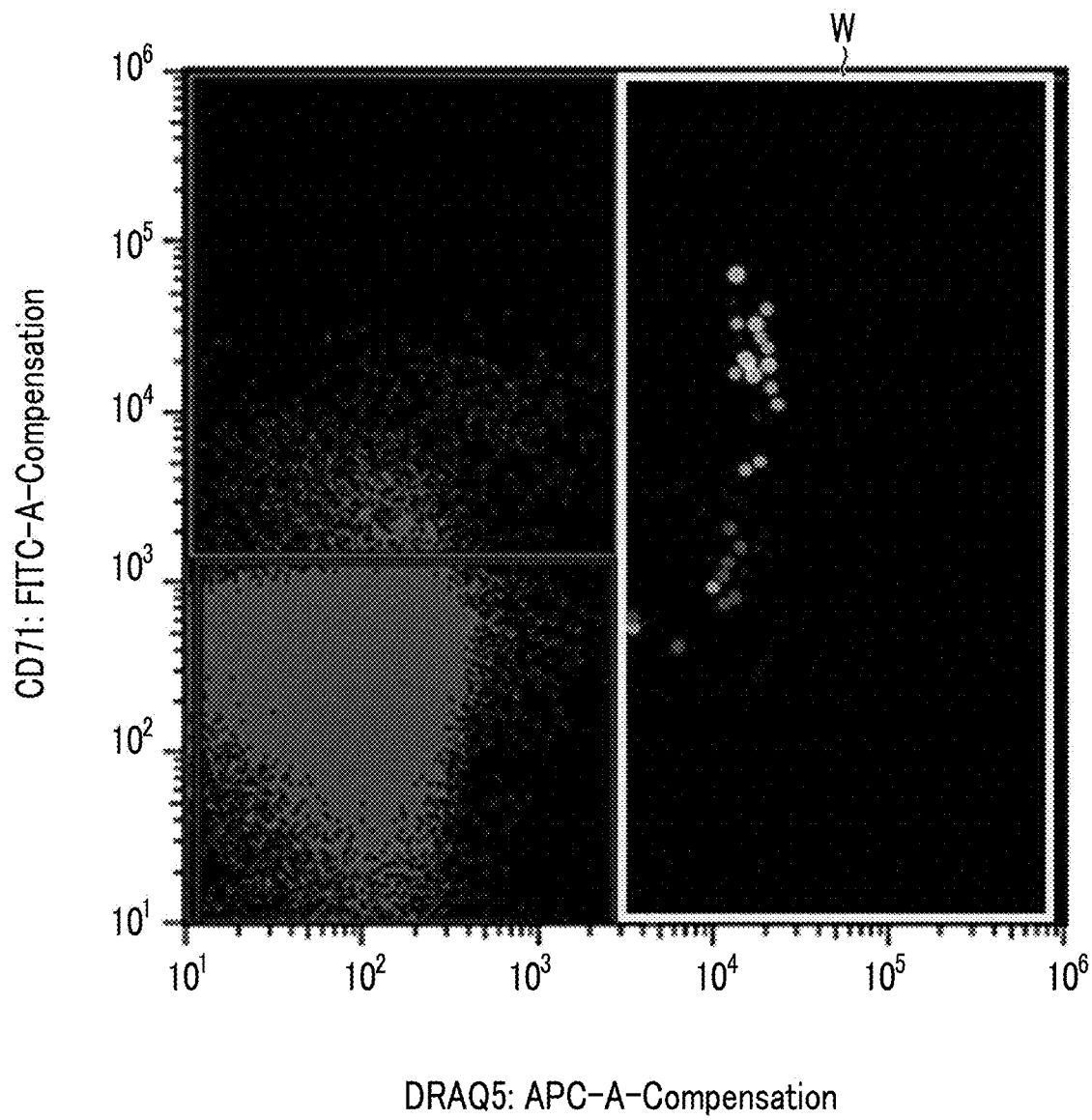
FIG. 5 is a scattergram in which the fluorescence intensity of FITC is plotted on the ordinate and the fluorescence intensity of DRAQ5 is plotted on the abscissa.

FIG. 5 is a scattergram in which the fluorescence intensity of FITC is plotted on the ordinate and the fluorescence intensity of DRAQ5 is plotted on the abscissa. The fluorescence intensity of FITC reflects the information on the juvenility of erythrocytes, and the fluorescence intensity of DRAQ5 reflects the information on the nucleus. From these pieces of first information, what kind of cells exist can be assumed. Furthermore, by gating a region W on the scattergram, a group can be separated from all the cells or groups on the graph. In FIG. 5, by specifying the region W by gating, a group in which nucleated erythrocytes are assumed to exist is separated from other cells.

The cells in the region W specified by gating are sorted into the wells 202 of the container 20 as target cells.

The controller 120 stores the positions of the wells 202 containing cells and the first information derived from the cells by correlating the positions with the first information. The positions of the wells 202 containing the cells are preferably identified by the rows and columns marked in the container 20 and the identification label 206.

<Imaging Step>

In the imaging step, the cells sorted into the container are imaged. Imaging cells means that the image of the cells are captured, and also includes a case where foreign substances (dust and the like) that are practically not cells are imaged. In the imaging step, it is preferable to move the cells, which are sorted into the container 20, to the bottom surface of the wells by using a centrifuge, and to use an image capturing apparatus 30 for imaging. Examples of the image capturing apparatus 30 include a fluorescence microscope including an imaging device.

Figure 6:
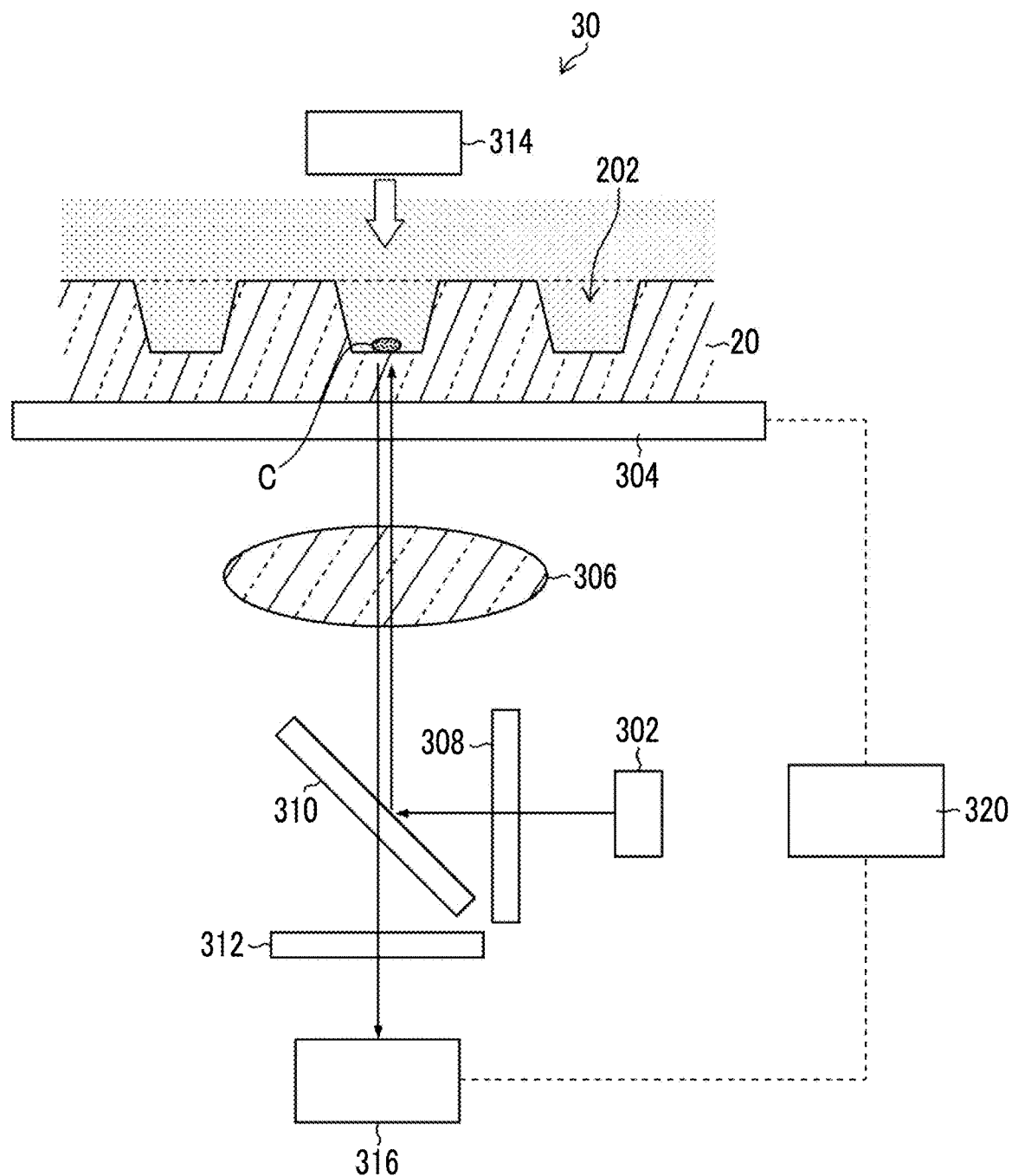
FIG. 6 is a view schematically showing the constitution of an image capturing apparatus.

FIG. 6 is a view schematically showing the constitution of the image capturing apparatus 30. The image capturing apparatus 30 can image cells C collected into the container 20. The image capturing apparatus 30 is constituted such that second information derived from cells can be obtained by imaging the cell C. The second information derived from cells include at least one of fluorescence, a cell shape, a transmitted color, or a size. The fluorescence means luminescence of the fluorescent label by immunostaining excited with excitation light. The transmitted color means a color generated by light transmitted through the cells.

In the present embodiment, a case will be described where the cells sorted into the container 20 are imaged from a side opposite to the opening of each of the wells 202 of the container 20 in the imaging step.

The image capturing apparatus 30 includes a first light source 302 for excitation that is for measuring fluorescence of the cell C, a table 304 for loading the container 20, a lens 306 spaced apart from the table 304 and disposed on a side opposite to the container 20, a filter group constituted with an excitation filter 308, a dichroic mirror 310, and a fluorescent filter 312, a second light source 314 which is disposed on the side of the well 202 of the container 20 and irradiates the container 20 with light for measuring transmitted light, and an imaging device 316 imaging the cell C.

The imaging device 316 is disposed in a position on the side opposite to the opening (front surface) of the well 202 of the container 20 into which the cell C is sorted. That is, the imaging device 316 can image the cell C from the rear surface of the container 20. The excitation light from the first light source 302 is radiated to the well 202 from the rear surface of the container 20, and the light from the second light source 314 is radiated to the well 202 from the front surface of the container 20.

In order for the container 20 to be irradiated with the excitation light from the rear surface side thereof or in order to transmit light and receive fluorescence from the cell and receive transmitted light, it is preferable that the material of the container 20 is transparent, is not autofluorescent, and does not scatter light.

Preferably, the image capturing apparatus 30 can obtain images by imaging the fluorescence emission from the cell C and bright-field images by capturing the image of light transmitted through the cell C.

As the first light source 302, for example, it is possible to use a high-pressure mercury lamp, a high-pressure xenon lamp, a light emitting diode, and a laser diode. As the first light source 302, it is also possible to use a tungsten lamp, a halogen lamp, a white light emitting diode, and the like. Even in a case where these light sources are used, only a target wavelength can be transmitted through the excitation filter 308. The immunostained cell C can be irradiated with light having a target excitation wavelength. As the second light source 314, the same light source as the first light source 302 can be used.

A case where the fluorescence intensity from the cell C is obtained as an image by the imaging device 316 will be described. Among the lights radiated from the first light source 302, only the light in a target wavelength range is transmitted through the excitation filter 308. The light transmitted through the excitation filter 308 is reflected toward the container 20 by the dichroic mirror 310. The light reflected by the dichroic mirror 310 is transmitted through the lens 306 and radiated to the cell C collected in the well 202. The light radiated to the cell C is in a wavelength range exciting the immunostained cell C. The immunostained cell C is excited by the excitation light and emits fluorescence of a wavelength different from the excitation wavelength radiated. The fluorescence from the cell C passes through the lens 306, the dichroic mirror 310, and the fluorescent filter 312 and imaged by the imaging device 316, and in this way, an image is obtained. The obtained image of the fluorescence is input and stored in a controller 320 as the second information. The wavelength of the fluorescence emitted by the excitation light is longer than the wavelength of the excitation light. Therefore, by the dichroic mirror 310, the light of the wavelength of the excitation light can be reflected toward the container 20 side, and the light of the wavelength of the fluorescence can be transmitted toward the imaging device 316 side. Furthermore, the fluorescent filter 312 can transmit only the fluorescence without transmitting the excitation light. Accordingly, in the imaging device 316, the cell C emitting fluorescence can be imaged. Because the fluorescent filter 312 transmits only the fluorescence, the image captured by the imaging device 316 is not affected by the excitation light. Consequently, an accurate image can be obtained.

The image capturing apparatus 30 of the present embodiment has the table 304 and a driving device (not shown in the drawing) for moving the container 20 to any position (for example, in the X direction, the Y direction, or the Z direction). By the table 304 and the driving device, a specific well 202 in the container 20 can be moved to an observation position. It is preferable that the driving device can move the table 304 in the X direction, the Y direction, and the Z direction.

In a case where the cell C is stained with a plurality of staining species, by the switching between different filter groups (the excitation filter 308, the dichroic mirror 310, and the fluorescent filter 312), images having different fluorescence wavelengths can be obtained.

In a case where the light transmitted through the cell C by the second light source 314 is imaged, imaging is performed in a state where the filter group is removed. In a case where the transmitted light is imaged using the imaging device 316, a bright-field image can be obtained. The obtained bright-field image is input and stored in the controller 320.

The imaging device 316 is not particularly limited as long as it can image the fluorescence of the cells in the wells 202 of the container 20 or can image the transmitted light. As the imaging device 316, for example, a charge-coupled device (CCD) camera can be used.

In the present embodiment, the image capturing apparatus 30 has been described in which the imaging device 316, the first light source 302, and the filter group are disposed on the rear surface side of the container 20 while the second light source 314 is disposed on the front surface side of the container. The present invention is not limited thereto, and an image capturing apparatus 30 can also be used in which the imaging device 316, the first light source 302, and the filter group are disposed on the front surface side of the container 20 while the second light source 314 is disposed on the rear surface side of the container.

<Determination Step>

In the determination step, based on the images of the cells captured by the imaging step, the second information derived from cells is obtained, and cells to be analyzed are determined from the cells sorted into the container 20. As described above, in the flow cytometry, cells are sorted based on the obtained optical information. Accordingly, dust or cells that are not target cells are collected into the wells in some cases. By obtaining the second information derived from cells and determining the cells to be analyzed, it is possible to rule out duet or cells that are not target cells. As a result, it is possible to effectively and accurately perform gene analysis only on target cells. For target cells and non-target cells, information such as the fluorescence intensity, the roundness of the cells, the color generated by the light transmitted through the cells, and the size of the cells can be obtained in advance. From the obtained information, a range showing a probability that a certain cell is a target cell can be determined, a threshold representing the range can be determined, and the threshold can be determined as a target cell to be analyzed. Various information obtained in this way can be used as the second information derived from cells. For example, in a case where nucleated erythrocytes and the like are target cells, it is possible to use various information in the sorting method described in WO2016021309A or WO2016021311A.

Figure 7:
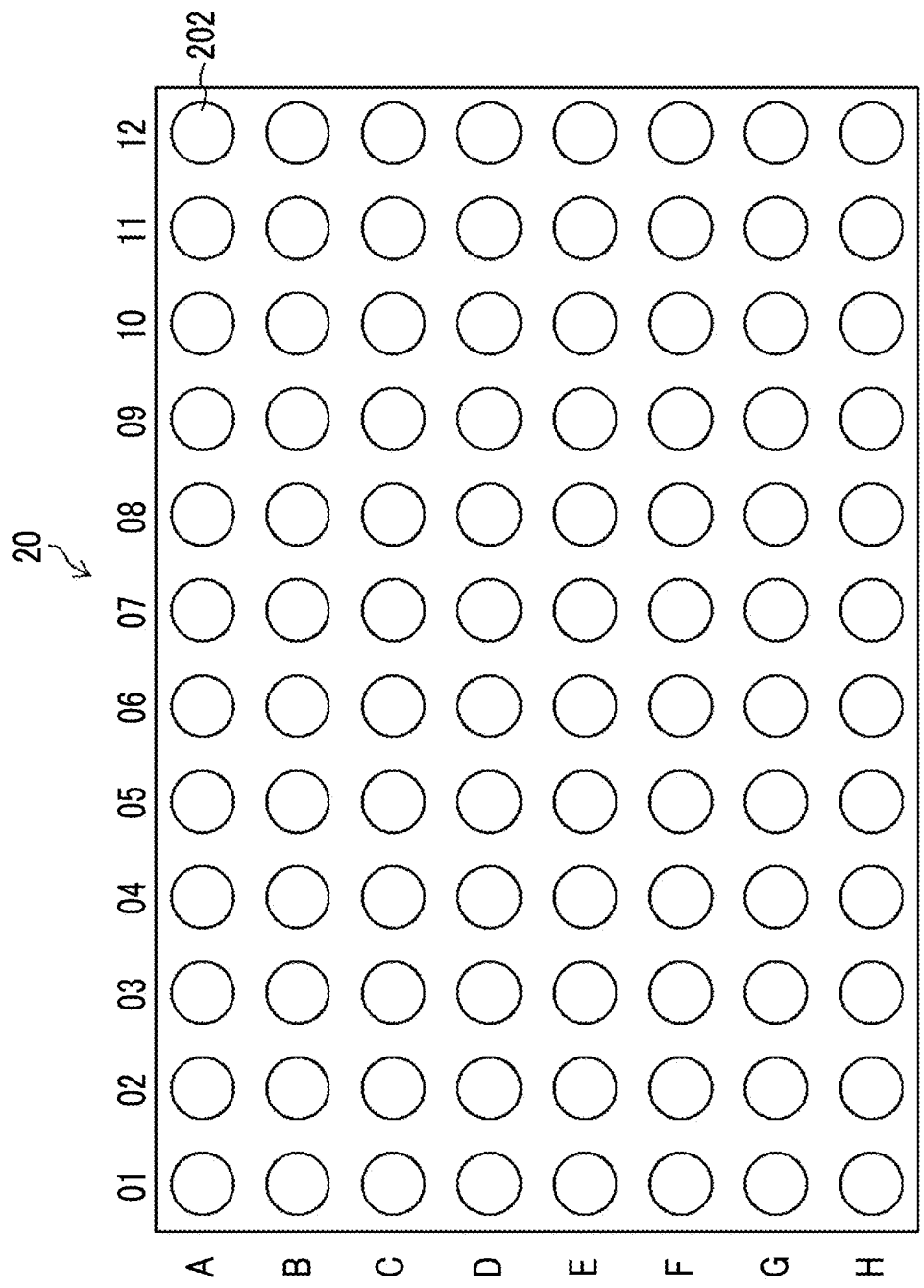
FIG. 7 is a plan view of a container having undergone a sorting step.

FIG. 7 is a plan view of a container having undergone the sorting step. The cells in the region W gated in the scattergram shown in FIG. 5 are sorted into the wells 202 of the container 20.

FIG. 8 is a plan view of the container 20 having undergone the imaging step. In the imaging step, cells in all of the wells 202 of the container 20 are imaged. In FIG. 8, some of the captured images are shown. Specifically, the images of a well A12, a well D12, a well G12, a well H03, a well H08, and a well H12 are shown. The second information derived from cells based on the images includes fluorescence, a cell shape, and a size.

As shown in FIG. 8, it is confirmed that the images of the well A12, the well D12, and the well G12 include nucleated erythrocytes. In contrast, in the images of the well H03, the well H08, and the well H12, a nucleated erythrocyte is not confirmed, and only dust or cell fragments can be confirmed. From these results, the cells in the well A12, the well D12, and the well G12 can be determined as cells that should be analyzed.

In reality, based on the images of the cells, the second information derived from cells is obtained, and all the wells are checked. FIG. 9 is a plan view of the container 20 in which the wells 202 containing the cells that should be analyzed are colored. As shown in FIG. 9, it is understood that the cells sorted into 63 wells 202 in the container 20 having 96 wells 202 are determined as cells that should be analyzed.

At the time of determining cells that should be analyzed, it is preferable that the positions of the plurality of wells 202 and the first information that are correlated with each other in the sorting step are correlated with the second information obtained in the imaging step. By correlating the positions of the wells 202 and the first information with the second information, for example, the first information and the second information can be read out from the positions of the wells 202 before performing the gene analysis. From the first information and the second information, it is possible to check whether or not the cells are cells that should be analyzed. Accordingly, it is possible to prevent the gene analysis from being incorrectly performed.

The positions of the wells 202, the first information, and the second information can be correlated with each other, for example, by the transmission and reception of relevant information through a network between the controller 120 of the flow cytometer 10 and the controller 320 of the image capturing apparatus 30, and the like.

As described above, in a case where the cells that should be analyzed are determined based on the first information obtained by the flow cytometry method and the second information obtained in the imaging step, it is possible to effectively and accurately perform gene analysis only on the target cells.

<Isolation Step>

It is preferable that the cell detection method further includes an isolation step of isolating only the cells to be analyzed from the container 20 after the determination step. By isolating only the cells to be analyzed and then performing gene analysis or a pre-treatment, the time taken for the gene analysis can be shortened. Herein, "isolating only the cells" means a case where only the cells are isolated but other components such as the culture solution is not isolated or a case where target cells are isolated together with the culture solution present in the periphery of the cells.

As the method for isolating only the cells to be analyzed from the container 20, several methods can be exemplified.

As a first method, the cells that should be analyzed can be aspirated into a capillary or a pipette from the wells 202 of the container 20 and moved to a plate for PCR or a tube for PCR. Specifically, as the container, it is possible to use a gravity trap-type well plate (for example, having a 1 mmφ bottom surface) manufactured by InSphero. Furthermore, it is preferable that a bar code is assigned to the side wall of the plate for PCR or the tube for PCR, and the first information and the second information are correlated with the positional information of the plate for PCR or the tube for PCR.

It is preferable that the culture solution contains a staining solution which is added for inhibiting a reduction in fluorescence in the imaging step. In this case, a side effect such as a hindrance to gene amplification is caused in the amplification step. Accordingly, it is preferable that the culture solution is substituted with a culture solution containing no staining solution after imaging.

In a preferred aspect, as a culture solution, 40 μL of a 0.1% by mass BSA-PBS solution to which DRAQ5 is added at 0.1 μmol/L is put into the container, cells are sorted and imaged by flow cytometry, 36 μL of the solution is discarded, 36 μL of 0.1% by mass BSA-PBS solution is put into the container, and then 36 μL of the solution is discarded again. After this operation is repeated twice, finally, the remaining 4 μL of the solution is preferably aspirated into a capillary or a pipette together with the cells contained in the solution and moved to a tube for PCR. As the capillary, it is preferable to use a capillary which has a distal end diameter of about tens of micrometers to 100 μm and is made of glass. As the pipette, it is preferable to use a pipette which has a distal end external diameter equal to or greater than 100 micrometers and equal to or smaller than 1 mm and is mainly formed of an organic resin (polypropylene or the like).

In a case where the container 20, in which the plurality of wells 202 and the side walls 204 form an integral structure as shown in FIG. 3, is used, as a second method, for example, by cutting the container 20 so as to split the container and cutting out only the wells 202 containing target cells, only the cells that should be analyzed can be isolated. In order to easily cut the container, it is preferable to provide a perforated line and the like on the surface of the container 20. The wells 202 cut out can be moved to a plate for PCR.

In a case where the container 20 constituted with a plurality of tubes 208 and the supporting member 210 as shown in FIG. 4 is used, as a third method, by cutting out only the tubes 208 containing target cells, only the cells that should be analyzed can be isolated. The tubes 208 cut out can be moved to a plate for PCR. Hitherto, examples of the method for isolating only the cells to be analyzed from the container 20 have been illustrated, but the method is not limited thereto.

Next, the amplification and the gene analysis performed on the isolated cells will be described by illustrating a case where nucleated erythrocytes are target cells.

In the amplification step, the nucleic acid contained in the chromosome of the nucleated erythrocytes, which are cells isolated from the container 20 or contained in at least the chromosome of fetal nucleated erythrocytes is amplified.

In a whole genome amplification method, the obtained cells go through cell lysis using a surfactant that is a general method and a proteolysis step using protease K or the like, and genomic DNA eluted from the cells in this way is used.

As reagents for the whole genome amplification, it is possible to use a reagent PicoPLEX WGA kit (manufactured by New England Biolabs.) based on a polymerase chain reaction (PCR), a GenomePlex Single Cell Whole Genome Amplification kit (manufactured by Sigma-Aldrich Co. LLC.), and reagents relating to a multiple annealing and looping-based amplification cycles (MALBAC) method disclosed in WO2012/166425A2. Furthermore, as reagents based on a strand displacement-type DNA synthesis reaction, for example, it is also possible to use GenomiPhi (manufactured by GE Healthcare, GenomiPhi is a registered trademark) and REPLI-g (manufactured by QIAGEN, REPLI-g is a registered trademark). In the present embodiment, it is preferable to use the PicoPLEXWGA kit (manufactured by New England Biolabs.).

For the DNA amplification product obtained by the whole genome amplification method, whether or not the DNA is amplified can be checked by agarose gel electrophoresis and the like. In addition, it is preferable to purify the whole genome amplification product by using a QIAquickPCR purification kit (manufactured by QIAGEN).

It is preferable that the concentration of the DNA amplification product obtained by the whole genome amplification method is measured using NanoDrop (manufactured by Thermo Fisher Scientific Inc.), Quantus Fluorometer (manufactured by Promega Corporation), BioAnalyzer (manufactured by Agilent Technologies), or TapeStation (manufactured by Agilent Technologies).

As the gene analysis, a DNA microarray method, a digital PCR method, a next-generation sequencer method, or nCounter System (manufactured by NanoString Technologies, Inc.) can be used. In the present embodiment, in view of the accuracy and speed of the analysis, the number of samples that can be treated at a time, and the like, it is preferable to use a next-generation sequencer method.

The DNA microarray method is a method of arraying DNA fragments of cells on a substrate at high density, performing hybridization on the DNA arrays on the substrate, and analyzing the genetic information expressed in the cells.

The digital PCR method is a method of distributing a target sample into a plurality of wells, performing individual PCR processes in parallel, and counting the number of positive reactions at the end of amplification.

In the present embodiment, the next-generation sequencer means a sequence classified as a sequencer contrasted with a capillary sequencer (referred to as a first-generation sequencer) using the Sanger's method. The next-generation sequencer includes a second generation, a third generation, a fourth generation and sequencers that will be developed in the future. Currently, the most widespread next-generation sequencer is a sequencer using a principle of determining a base sequence by measuring fluorescence or luminescence related with the synthesis of a complementary strand by a DNA polymerase or the binding of a complementary strand by a DNA ligase. Specifically, examples thereof include MiSeq (manufactured by Illumina, Inc.), HiSeq 2000 (manufactured by Illumina, Inc., HiSeq is a registered trademark), Roche 454 (manufactured by Hoffmann-La Roche Ltd), and the like.

In a case where the DNA amplification product obtained in the amplification step is analyzed using the next-generation sequencer, it is possible to use whole genome sequencing, exome sequencing, and amplicon sequencing.

Examples of means for aligning sequence data obtained by the next-generation sequencer include Burrows-Wheeler Aligner (BWA). It is preferable to map the sequence data to a known human genome sequence by using BWA. Examples of means for analyzing genes include SAMtools and BEDtools. It is preferable to analyze gene polymorphism, gene variant, and the number of chromosomes by using the analysis means.

In the present embodiment, a case where blood cells are used as cells has been illustrated, but the present invention is not limited thereto.

EXPLANATION OF REFERENCES

10: flow cytometer
20: container
30: image capturing apparatus
102: nozzle
104: flow cell
106: light source
108: detector
110: detector
112: deflection electrode plate
114: deflection electrode plate
120: controller
202: well
204: side wall
206: identification label
208: tube
210: supporting member
212: hole
302: first light source
304: table
306: lens
308: excitation filter
310: dichroic mirror
312: fluorescent filter
314: second light source
316: imaging device
320: controller
C: cell
L: sheath liquid
S: sample solution
S1, S2, S3: step
W: region

What is claimed is:

1. A cell detection method comprising:
   a sorting step of obtaining first information derived from cells in a sample solution and sorting target cells into a container having arrays of wells each having an opening based on the first information by using a flow cytometry method;
   an imaging step of imaging the target cells sorted into the wells of the container, wherein the imaging step is performed after sorting by the flow cytometry method; and
   a determination step of obtaining second information derived from the target cells based on the image of the target cells captured by an imaging apparatus and determining cells to be analyzed from the imaged target cells sorted into the wells of the container,
   wherein the sorting step comprises a step of correlating a position of each of the wells with the first information, and
   the determination step comprises a step of correlating the position of each of the wells and the first information that are correlated with each other with the second information and a step of determining the cells to be analyzed based on the second information relative to a predetermined threshold on information on the target cells and non-target cells.

2. The cell detection method according to claim 1, further comprising:
   a step of staining cells before the sorting step.

3. The cell detection method according to claim 2, wherein the container has arrays of a plurality of wells each having an opening.

4. The cell detection method according to claim 2, wherein the imaging step includes a step of moving the cells to a bottom surface of each of the wells by centrifugation.

5. The cell detection method according to claim 2,
wherein the imaging step includes a step of imaging the cells sorted into the container from a side opposite to the opening of each of the wells of the container.

6. The cell detection method according to claim 1,
wherein the container has arrays of a plurality of wells each having an opening.

7. The cell detection method according to claim 6,
wherein the imaging step includes a step of moving the cells to a bottom surface of each of the wells by centrifugation.

8. The cell detection method according to claim 1,
wherein the imaging step includes a step of moving the cells to a bottom surface of each of the wells by centrifugation.

9. The cell detection method according to claim 1,
wherein the imaging step includes a step of imaging the cells sorted into the container from a side opposite to the opening of each of the wells of the container.

10. The cell detection method according to claim 1,
wherein the first information comprises at least one of forward-scattered light, side-scattered light, or fluorescence, and
the second information comprises at least one of fluorescence, a cell shape, a transmitted color, or a size.

11. The cell detection method according to claim 1,
wherein the sample solution contains blood cells.

12. The cell detection method according to claim 1,
wherein the wells of the container are arrayed in rows and columns.

13. The cell detection method according to claim 1,
further comprising;
an isolation step of isolating only the cells to be analyzed from the container after the determination step.

14. The cell detection method according to claim 13,
wherein in the isolation step, only the cells to be analyzed are isolated using a capillary or a pipette.

15. The cell detection method according to claim 13,
wherein the cells isolated in the isolation step are moved to a tube for polymerase chain reaction (PCR) or a plate for PCR.

16. The cell detection method according to claim 15,
wherein the first information and the second information are correlated with positional information of the tube for PCR or the plate for PCR.

17. The cell detection method according to claim 1,
wherein the wells of the container contain a culture solution in the interior thereof.

18. The cell detection method according to claim 17,
wherein the culture solution contains at least one staining solution.

19. The cell detection method according to claim 18,
further comprising:
a step of substituting the culture solution with a culture solution containing no staining solution after the imaging step.

20. The cell detection method of claim 1, wherein in the determining step, the step of correlating the position of each of the wells and the first information results in a first correlation, and the second information correlated with the first correlation is compared to the predetermined threshold in the step of determining cells to be analyzed.

* * * * *